United States Patent [19]

Van Der Puy et al.

[11] 4,374,289

[45] Feb. 15, 1983

[54] PRODUCTION OF MONOFLUOROTRICHLOROETHANE

[75] Inventors: Michael Van Der Puy; Ronald F. Piskorz, both of Cheektowaga, N.Y.

[73] Assignee: Allied Corporation, Morris Township, Morris County, N.J.

[21] Appl. No.: 313,535

[22] Filed: Oct. 22, 1981

Related U.S. Application Data

[62] Division of Ser. No. 192,770, Oct., 1980, abandoned.

[51] Int. Cl.$^3$ ............................................. C07C 17/00
[52] U.S. Cl. ................................. 570/168; 570/166; 570/165
[58] Field of Search ............................... 570/168, 166

[56] References Cited

U.S. PATENT DOCUMENTS 4,258,225 3/1981 Feiring ................................. 570/168

Primary Examiner—Charles F. Warren
Assistant Examiner—Joseph A. Boska
Attorney, Agent, or Firm—Jay P. Friedenson

[57] ABSTRACT

1-Fluoro-1,1,2-trichloroethane is produced by a process which comprises the reaction of trichloroethylene with hydrogen fluoride using about 1.5 to 3.5 moles of hydrogen fluoride per mole of trichloroethylene, and conducting the reaction in the presence of a catalyst selected from the group consisting of $CF_3SO_3H$, $TiCl_4$, $MoCl_5$, $WF_6$, $NbCl_5$ and $SnCl_4$ at a temperature in the range of 50° to 150° C. with a residence time of one quarter hour to five hours. The resulting product is relatively pure of overfluorinated by-products so as to be useful as a degreasing solvent.

4 Claims, No Drawings

PRODUCTION OF MONOFLUOROTRICHLOROETHANE

This is a division, of application Ser. No. 192,770, filed Oct. 1, 1980, now abandoned.

TECHNICAL FIELD

This invention relates to methods for the production of monofluorotrichloroethane by hydrofluorination of trichloroethylene in the presence of a catalyst, and more particularly to a method for the production of monofluorotrichloroethane by the reaction with hydrogen fluoride under moderate reaction conditions with the substantial elimination of multi-fluorinated compounds.

Background Art

The fluorination of unsaturated hydrocarbons such as trichloroethylene and tetrachloroethylene by reaction with hydrogen fluoride is known in the prior art. The reaction has been conducted using various catalytic materials with the production of a variety of mono- and polyfluorinated compounds. The reaction presents possibilities for both addition and substitution reactions so that the prior art indicates that the reaction often results in the production of a mixture of fluorinated compounds. For example, when hydrogen fluoride is reacted with trichloroethylene, monofluoro- and any of a series of polyfluoro compounds can be produced through addition of fluorine to the compound and substitution of fluorine for hydrogen and/or chlorine in the compound. Usually, a number of these reactions all occur so that often a mixture of several products is obtained. Obtaining a mixture of similar products is, of course, unsatisfactory because efficiency and yields of the conversion are reduced and the desired product is often difficult to separate the recover as a pure product.

A desirable product from the reaction of trichloroethylene with hydrogen fluoride is 1,1,2-trichloro-1-fluoroethane, but synthesis of this material by this method in an efficient and high yield manner has been difficult to achieve in the prior art. The main problem is that the hydrogen fluoride alone reacts slowly with the trichloroethylene thereby necessitating the use of high temperatures in the range of 200° to 300° C. under autoclave conditions at high pressures typically on the order of up to 1,000 psi. Such conditions have been necessary in order to realize good conversions at a convenient time period. The data available in the literature suggests that in this reaction, however, the addition of hydrogen fluoride to trichloroethylene is accompanied by varying amounts of halogen exchange giving rise to other products. This additional fluorination is difficult to avoid since at the temperatures required to add hydrogen fluoride to trichloroethylene, the exchange reactions also occur. If such further fluorination is not desired, it therefore represents a yield loss since it is not readily possible to convert the over-fluorinated materials back into the desired products.

Various catalytic materials have been known in the art for conducting processes of this type and the data shown in the prior art suggests that the activity of most catalysts is totally unpredictable with respect to the product desired to be produced. Thus, in the literature article by A. L. Henne et al, *Journal of American Chemical Society*, Volume 70, pages 758–760 (1948), it is reported that an improved reaction between trichloroethylene and HF takes place in the presence of small quantities of boron fluoride. However, the results appeared to be unpredictable as the results were mixed, there being no reaction at 160° C. for 12 hours.

U.S. Pat. No. 2,622,106 to Stover refers to the work of Henne et al with the indication that the prior art always obtained mixtures of the indicated products. In this patent, monofluorochloroalkanes are produced using an excess of hydrogen fluoride under pressure at temperatures of 175° to 325° C. and in the absence of a catalyst. Nevertheless, the results shown in this patent indicate that mixtures of fluorinated products are obtained as may be seen in Tables 1 and 2.

McBee et al, *Ind. Eng. Chem.*, Volume 39, pages 409–412 (1947), used antimony pentachloride as a catalyst in the conversion of trichloroethylene to 2-chloro-1,1,1-trifluoroethane and 1,2-dichloro-1,1-difluoroethane with hydrogen fluoride at temperatures of about 170° to 228° C., but mixtures of products were obtained rather than a substantial amount of any one product. Similarly, in the work of Scipioni et al, *Chemical Abstracts*, Volume 68, page 104493H (1968), trichloroethylene is reacted with hydrofluoric acid and $SbCl_5$ in the liquid phase at 130° C. for three hours from which some 33 products were isolated, four of which were yields of above 1%.

In U.S. Pat. No. 4,078,007 to Ferstandig, there is disclosed the reaction of a trichloroalkane with liquid hydrogen fluoride in the presence of a mixture of pentahalide with at least an equal amount of antimony trihalide which again results in the mixture of products by a substitution reaction. Further, U.S. Pat. No. 2,560,838 describes the reaction of hydrogen fluoride and olefinic compounds using boron trifluoride as a catalyst. U.S. Pat. No. 2,637,747 to McBee is similar to the McBee et al article described above in which trichloroethylene is reacted with HF either without a catalyst or in the presence of $SbCl_5$ to improve the efficiency of the reaction. A similar disclosure may be found in U.S. Pat. No. 2,724,004 to Frederick wherein antimony pentachloride is employed as a catalyst to produce 1,1-difluoro-1,2,2-trichloroethylene from tetrachloroethylene and HF at reaction temperatures of 100° to 250° C.

In an article by A. E. Feiring, *Journal of Fluorine Chemistry*, Volume 13, pages 7–18 (1979), the chemistry of hydrogen fluoride reactions with tetra- and trichloroethene were studied in connection with the use of various catalysts for the reaction. The catalysts studied included $BF_3$, $TaCl_5$, $Ta_2O_5$, $CoF_3$, $V_2O_5$, $ZrCl_4$, $NbCl_5$, $HgO$, $WCl_6$, $TiCl_4$, $MoCl_5$, $SbCl_5$, $TaF_5$ and $NbF_5$. In this publication it was concluded that $TaF_5$, $NbF_5$, $TiCl_4$ and $MoCl_5$ catalyzed the reaction and $TaF_5$ appeared to be the most active of the catalysts. However, observations were made that antimony pentachloride was inactive at temperatures as low as 75° C. and that addition reactions of HF to tetrachloroethylene showed no activity of 150° C. using the catalysts $BF_3$, $TaCl_5$, $Ta_2O_5$, $CoF_3$, $V_2O_5$, $ZrCl_4$, $NbCl_5$, $HgO$ and $WCl_6$. The experimental results in this publication, however, further indicated that mixtures of products were normally obtained rather than pure products which were not contaminated with either starting material or different fluorinated reaction products.

The present invention provides a method for the production of a monofluoro substituted trichloroethane in good yield without substantial contamination by starting materials or other products, which reaction thus represents a clear advance over the processes known to the prior art.

SUMMARY OF THE INVENTION

It is accordingly one object of this invention to provide a method for the production of monofluorinated trichloroethanes by the reaction of hydrogen fluoride and trichloroethylene.

A further object of the present invention is to provide a method for the production of monofluorotrichloroethane by the reaction of hydrogen fluoride with trichloroethylene in the presence of a select group of catalytic reagents and under moderate reaction conditions.

A still further object of the present invention is to provide a method for the production of 1-fluoro-1,1,2-trichloroethane by the reaction of hydrogen fluoride with trichloroethylene in the presence of a select group of catalytic materials wherein production of overfluorinated by-products is minimized and the product is obtained in good yield without substantial contamination by starting materials or other fluorinated products.

Other objects and advantages of the present invention will become apparent as the description thereof proceeds.

In satisfaction of the foregoing objects and advantages there is provided by this invention a method for the production of monofluorotrichloroethane which comprises the reaction of trichloroethylene and hydrogen fluoride using at least 1.5 to 3.5 moles of hydrogen fluoride per mole of trichloroethylene in the reaction, and conducting said reaction in the presence of a catalytic material selected from the group consisting of trifluoromethane sulfonic acid, titanium tetrachloride, molybdenum pentachloride, tungsten hexafluoride, niobium pentachloride, and stannous tetrachloride, in the temperature range of 50° to 150° C. and with a residence time of one-fourth hour to five hours.

Best Mode for Carrying Out the Invention

The present invention provides a method for the production of monofluoro-substituted trichloroethanes by the reaction with hydrogen fluoride with trichloroethylene in the presence of certain catalytic materials and under certain reaction conditions. It has been found according to this invention that excellent yields of desired products can be obtained without substantial contamination from the formation of other fluorinated products, but with sufficient conversion of starting material that the fluorinated products can be easily separated from the trichloroethylene feedstock. The reaction is conducted under moderate temperature conditions in order to avoid overfluorination, but yet with sufficient temperature conditions and the use of certain catalytic materials which enable good conversions to the desired product.

The starting material employed in the present invention is trichloroethylene, a known compound. This compound is reacted with hydrogen fluoride under the conditions of the reaction to yield 1-fluoro-1,1,2-trifluoroethane. The amount of hydrogen fluoride required for the reaction is in the range of about 1.5 to 3.5 moles of hydrogen fluoride per mole of trichloroethylene. It has been found that this amount of hydrogen fluoride is necessary to effect the necessary conversions under the moderate reaction conditions employed but is insufficient to cause the production of overfluorinated products.

The product produced as a result of the process of this invention is 1-fluoro-1,1,2-trichloroethane, which is useful as a degreasing solvent. Use as a degreasing solvent is as well known for 1,1,2-trichlorotrifluoroethane.

The reaction is conducted in the presence of a catalytic material and preferably a select group of catalytic materials in specified amounts in order to provide the necessary conversions. The catalytic materials which have been found to be reactive to provide the necessary conversions in the present invention are those selected from the group consisting of trifluoromethane sulfonic acid, titanium tetrachloride, molybdenum pentachloride, tungsten hexafluoride, niobium pentachloride, stannous tetrachloride, and mixtures thereof. Certain of these catalytic materials are disclosed in the prior art as having been used in similar reactions as may be seen from the above discussion. However, none of these catalytic materials appear to have been employed in the prior art to produce the compound of this invention from trichloroethylene under moderate conditions of time and temperature. In fact, as noted in the publication by Feiring, *J. of Fluorine Chem.*, Vol. 13, pgs. 7–18 (1979), certain similar catalysts such as $NbCl_5$ and $WCl_6$ showed no catalytic activity at 150° C. for the addition reaction of hydrogen fluoride to tetrachloroethylene. Contrary to these teachings of the prior art, the present invention provides a select group of conditions under which all of the above-listed catalytic materials are reactive to produce the compound of this invention by reaction with trichloroethylene. The catalyst is employed in amounts ranging from about 0.05 to 0.2 moles of catalytic material per mole of trichloroethylene to be employed in the reaction.

As indicated above, the reaction conditions for the process of this invention are moderate, that is, the temperature ranges from about 50°–150° C. with a residence or contact time with the catalyst being about one-fourth hour to five hours. The temperature and residence time will, of course, vary within these limits depending on the catalytic material employed as will be apparent from the experimental results set forth hereinafter.

A preferred mode for conducting the reaction is to initially contact the catalyst and hydrogen fluoride under pressure and under a nitrogen atmosphere at very low temperatures. Hydrogen fluoride is extremely corrosive material and must be handled carefully. Accordingly, in the preferred process of this invention, the catalyst and hydrogen fluoride are contacted under the nitrogen atmosphere in the pressure reactor under very low temperatures to allow any reaction to occur between the catalyst and the hydrogen fluoride. Normally, since the catalysts are chloride or sulfonic acid derivatives, there may be a reaction between the hydrogen fluoride and catalyst with evolution of HCl or $SO_2$ which may be vented to maintain a desired pressure. After this reaction is completed, the resulting mixture is then warmed to the temperature within the range of 50° to 150° C. and the trichloroethylene is added to the reactor. The pressure within the reactor is preferably maintained at about 175 to 250 psig and preferably about 200±10 psig by venting gases in excess of this pressure.

After the residence time for the reaction is completed, the contents of the vessel are chilled, the pressure is vented, and the contents of the vessel recovered with the organic layer separated and dried.

The following examples are presented to illustrate the invention but are not considered to be limited thereto. In these examples and throughout the specification, parts are by weight unless otherwise indicated.

EXAMPLES 1-11

The following experiments were carried out in a small (150 ml) stainless steel cylinder equipped with a pressure gauge and vent valve. This cylinder was connected to a second (75 ml) cylinder via a ball valve. The catalyst was charaged to the vessel under a nitrogen atmosphere. The vessel was then chilled to −78° C. and evacuated. HF was added, and the mixture allowed to warm to room temperature. The gases generated by the reaction of HF with the catalyst was then vented. After warming the contents of the vessel to the temperature specified in the Table by immersing the 150 ml cylinder into a thermostated oil bath, trichloroethylene was added from the second cylinder. The pressure within the reactor was limited to 200±10 psig by venting gases generated in excess of this pressure. The vented gas passed through a water scrubber, drier tower and a −78° C. cold trap.

After the end of the allotted time shown in the Table, the contents of the vessel were chilled in ice, and the pressure in excess of atmospheric was vented as before. The contents of the vessel were carefully poured onto ice and the organic layer separated and dried over $Na_2SO_4$. Analysis of the product mixture (including contents of the cold trap) was made by gas chromatography using ⅛″×10′ columns of 10% OV-101 on Chromosorb W and Porapak Q.

The parameters and reactions of the experiments are set forth in the following Table 1. In this table are set forth the type of catalyst employed for each example, the reactants in moles for each of the materials reacted, the conditions for the reaction, including residence time and temperature. In Table 2 are set forth the products recovered, including other fluorinated products, starting material and total weight of organic material recovered. In the tables, TCE means trichloroethylene starting material, product I is the 1-fluoro-1,1,2-trichloroethane product of this invention, product II is 1,1-difluoro-1,2-dichloroethane and product III is trifluoromonochloroethane. The other product is a tetrachloroethane product with minor amounts of unidentified materials.

TABLE 1

Preparation of 1,1,2-Trichloro-1-fluoroethane from Trichloroethylene

| Exp. | Catalyst | Reactants (Moles) Cat. | HP | TCE | Conditions |
|---|---|---|---|---|---|
| 1 | $CF_3SO_3H$ | .032 | 1.035 | .494 | 4 h, 130° C. |
| 2 | $TiCl_4$ | .033 | 1.135 | .499 | 2.4 h, 100° C. |
| 3 | $MoCl_5$ | .029 | 1.18 | .498 | 15 min, 100° C. |
| 4 | $MoCl_5$ | .031 | .965 | .499 | 25 min, 82° C. 25 min, 100° C. |
| 5 | $MoCl_5$ | .089 | 1.56 | .519 | 1 h, 100° C. |
| 6 | $WF_6$ | .034 | 1.46 | .497 | 1.25 h, 100–120° C. |
| 7 | $NbCl_5$ | .030 | .915 | .501 | 40 min, 50° C. 1 h, 85° C. |
| 8 | $MoCl_5$ | .032 | 1.175 | .496 | 1 h, 100° C. |
| 9 | $SnCl_4$ | .031 | 1.21 | .506 | 7 h, 100° C. |
| 10 | $SnCl_4$ | .033 | 1.46 | .503 | 1 h, 110° C. |
| 11 | $SnCl_4$ | .153 | 1.60 | .496 | 2.6 h, 110° C. |

TABLE 2

| Exp. | TCE | I | II | III | $CH_2ClCCl_3$ | Other | Wt. (g) Org. Recovered |
|---|---|---|---|---|---|---|---|
| 1 | 29.4 | 69.3 | 0.2 | — | — | 1.1 | 69.1 |
| 2 | 10.3 | 84.5 | 2.2 | — | — | 2.7 | 71.1 |
| 3 | 53.0 | 44.4 | 1.0 | — | 1.6 | — | 65.0 |
| 4 | 9.2 | 78.3 | 8.6 | — | 3.1 | 0.7 | 71.8 |
| 5 | 8.8 | 83.4 | 4.6 | tr | 2.9 | 0.3 | 68.6 |
| 6 | 16.7 | 80.5 | 0.3 | — | — | 2.3 | 70.4 |
| 7 | 5.2 | 73.9 | 2.8 | — | 6.2 | 11.9 | 68.6 |
| 8 | 4.7 | 64.6 | 24.7 | — | 5.8 | 0.3 | 67.9 |
| 9 | 32.5 | 47.7 | 19.6 | tr | 0.2 | — | 67.2 |
| 10 | 67.5 | 28.4 | 3.9 | — | 0.2 | — | 65.2 |
| 11 | 37.5 | 45.7 | 16.0 | — | 0.7 | — | 64.4 |

As will be seen from the table, excellent results are achieved in production of the desired 1-fluoro-1,1,2-trichloroethane although some catalysts are more active than others. For instance, $MoCl_5$ in Example 3 at 15 minutes for 100° C. shows a minimum of overfluorinated products, whereas in Example 8, $MoCl_5$ at 100° C. for 1 hour converted most of the starting material but also formed a substantial amount of 1,1-difluoro-1,2-dichloroethane.

The invention has been described herein with reference to certain preferred embodiments. However, as obvious variations thereon will become apparent to those skilled in the art, the invention is not considered to be limited thereof.

We claim:

1. A method for the production of 1-fluoro-1,1,2-trichloroethane which comprises reacting trichloroethylene with hydrogen fluoride using about 1.5 to 3.5 moles of hydrogen fluoride per mole of trichloroethylene, and conducting the reaction in the presence of tungsten hexafluoride at a temperature range of about 50° to 150° C. for a residence time of about one-fourth hour to five hours.

2. A method according to claim 1 wherein about 2.0 to 3.0 moles of hydrogen fluoride are used per mole of trichloroethylene.

3. A method according to claim 1 wherein about 0.05 to 0.2 moles of catalyst are used per mole of trichloroethylene.

4. A method according to claim 1 wherein the reaction is conducted in pressure reactor under pressure of about 175 to 250 psig.

* * * * *